(12) United States Patent
Gold et al.

(10) Patent No.: US 8,692,021 B2
(45) Date of Patent: Apr. 8, 2014

(54) METHOD OF PREPARING NERAMEXANE OR A SALT THEREOF

(75) Inventors: Markus-Rene Gold, Karlstadt (DE); Valerjans Kauss, Riga (LV); Aigars Jirgensons, Riga (LV)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/498,432

(22) PCT Filed: Sep. 24, 2010

(86) PCT No.: PCT/EP2010/005864
§ 371 (c)(1),
(2), (4) Date: Jun. 6, 2012

(87) PCT Pub. No.: WO2011/035924
PCT Pub. Date: Mar. 31, 2011

(65) Prior Publication Data
US 2012/0245391 A1    Sep. 27, 2012

Related U.S. Application Data

(60) Provisional application No. 61/277,691, filed on Sep. 28, 2009.

(30) Foreign Application Priority Data

Sep. 28, 2009  (EP) .................................... 09012283

(51) Int. Cl.
*C07C 211/00*    (2006.01)

(52) U.S. Cl.
USPC ........................................... 564/462; 564/448

(58) Field of Classification Search
None
See application file for complete search history.

(56) References Cited

FOREIGN PATENT DOCUMENTS

WO    WO 2005062724 A2 *    7/2005

OTHER PUBLICATIONS

Aigars, Jirgensons, "The synthesis of carbocyclic amines—potential NMDA receptor antagonists", Summary of Dissertation, University of Latvia, Riga, 2000.
Chen, H.G.. et al, Tetrahedron Letters. vol. 37, No, 45, Nov. 4, 1956.
Danysz, W., et al. Current Pharmaceutical Design, vol. 8, No. 10, Jan. 1, 2002.
International Search Report for PCT/EP2010/005864 of Dec. 15, 2010.
Written Opinion of the International Searching Authority PCT/EP2010/005864 of Dec. 20, 2010.

* cited by examiner

*Primary Examiner* — Sudhakar Katakam
(74) *Attorney, Agent, or Firm* — Hueschen and Sage

(57) ABSTRACT

Method of preparing 1-amino-1,3,3,5,5-pentamethylcyclohexane or a pharmaceutically acceptable salt thereof (Neramexane), comprising step (iv):
(iv) hydrolyzing a mixture comprising an acid, 1-formamido-1,3,3,5,5-pentamethylcyclohexane and hydrogen cyanide to yield 1-amino-1,3,3,5,5-pentamethylcyclohexane.

18 Claims, No Drawings

METHOD OF PREPARING NERAMEXANE OR A SALT THEREOF

FIELD OF THE INVENTION

This invention relates to a method of preparing 1-amino-1,3,3,5,5-pentamethylcyclohexane (Neramexane) or a pharmaceutically acceptable salt thereof.

BACKGROUND OF THE INVENTION 1-amino-1,3,3,5,5-pentamethylcyclohexane (Neramexane) and pharmaceutically acceptable salts thereof are valuable agents for the continuous therapy of patients suffering from diseases and conditions such as tinnitus, and nystagmus.

Methods of preparing these agents are known.

In one method, commercially available isophorone is converted to Neramexane in a reaction sequence comprising five steps according to the reaction scheme below (W. Danysz et al., Current Pharmaceutical Design, 2002, 8, 835-843).

In the first step of the sequence, isophorone 1 is converted to 3,3,5,5-tetramethylcyclohexanone 2 by CuCl-catalyzed conjugate addition of methylmagnesium iodide;

in the second step, 3,3,5,5-tetramethylcyclohexanone 2 is converted to 1,3,3,5,5-pentamethylcyclohexanol 3 by Grignard reaction with methylmagnesium iodide;

in the third step, said cyclohexanol 3 is converted to 1-chloroacetamido-1,3,3,5,5-pentamethylcyclohexane 6 by chloroacetonitrile in a Ritter reaction;

In the fourth step, subsequent cleavage of the chloroacetamido group in amide 6 with thiourea, and acidification of the resulting amine with hydrochloric acid in the final fifth step of the reaction sequence results in Neramexane (1-amino-1,3,3,5,5-pentamethylcyclohexane) 7 in the form of its hydrochloride:

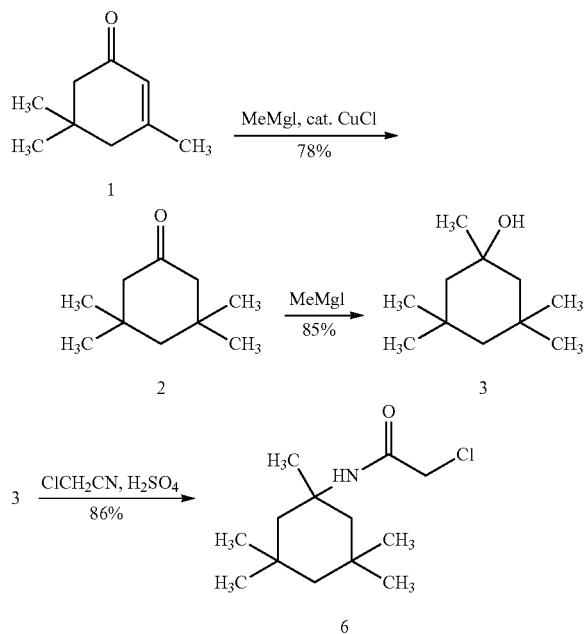

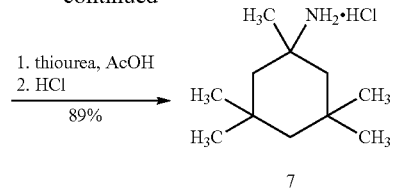

In one approach, acetonitrile has been used to form the respective 1-acetamido-1,3,3,5,5-pentamethylcyclohexane. Cleavage under basic conditions and prolonged heating in octanol resulted in 1-amino-1,3,3,5,5-pentamethylcyclohexane (A. Jirgensons, The Synthesis of Carbocyclic Amines—Potential NMDA Receptor Antagonists, Summary of Dissertation, University of Latvia, Riga, 2000).

In another approach, cyclohexanol 3 has been reacted with trimethysilyl cyanide (TMSCN) to yield the respective formamido compound 5. It has been established that TMSCN decomposes under the Ritter reaction conditions, and that hydrogen cyanide acts as the actual nitrile source:

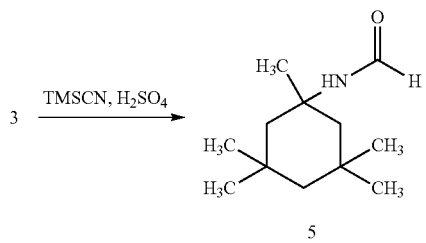

Cleavage of the formamido group in 5 under acidic conditions resulted in Neramexane (see A. Jirgensons as referenced above).

In still another approach, cyclohexanol 3 has been reacted with potassium cyanide to yield the respective formamido compound 5. Cleavage of the formamido group in 5 under acidic conditions resulted in Neramexane (see A. Jirgensons as referenced above).

The commonly accepted understanding of all these Ritter reactions is that starting from a tertiary alcohol such as cyclohexanol 3, under the influence of an acid a carbocation is generated in situ that reacts with the nitrogen atom of the nitrile respectively the cyanide component such as hydrogen cyanide, thus introducing the amino functionality at the respective tertiary carbon atom.

OBJECTS OF THE INVENTION

One object of the invention is to improve one or more of the known types of the Ritter reaction in the above referenced reaction sequence in order to provide a method of preparing 1-amino-1,3,3,5,5-pentamethylcyclohexane or a pharmaceutically acceptable salt thereof that allows an advantageous realization on an economical industrial scale. It is in another object to minimize the amount of waste and/or unused chemicals produced during the manufacture of Neramexane or a pharmaceutically acceptable salt thereof. It is a further object to optimize or improve the yield and/or selectivity and/or product quality in regard to Neramexane or a pharmaceutically acceptable salt thereof. Such an improved method may be regarded as one prerequisite for an advantageous manufacture of Neramexane or a pharmaceutically acceptable salt thereof on an economical industrial scale.

SUMMARY OF THE INVENTION

The present invention relates to a method of preparing 1-amino-1,3,3,5,5-pentamethylcyclohexane or a pharmaceutically acceptable salt thereof. Specifically, the invention relates to a method of optimizing one or more known types of the Ritter reaction in the third step of the above referenced reaction sequence.

More specifically, the invention relates to a method of preparing 1-amino-1,3,3,5,5-pentamethylcyclohexane or a pharmaceutically acceptable salt thereof, comprising step (iv):
  (iv) hydrolyzing a mixture comprising an acid, 1-formamido-1,3,3,5,5-pentamethylcyclohexane and hydrogen cyanide to yield 1-amino-1,3,3,5,5-pentamethylcyclohexane.

In one embodiment the method of the present invention comprises prior to step (iv) step (iii):
  (iii) reacting 1-hydroxy-1,3,3,5,5-pentamethylcyclohexane with hydrogen cyanide in the presence of said acid, or with a compound that forms hydrogen cyanide in the presence of said acid, to yield a mixture comprising said acid, 1-formamido-1,3,3,5,5-pentamethylcyclohexane and hydrogen cyanide.

In one embodiment, said compound that forms hydrogen cyanide in the presence of said acid is a salt of hydrogen cyanide, or is a cyano group-containing silicon compound.

In one embodiment, said salt of hydrogen cyanide is selected from ammonium cyanide, sodium cyanide, potassium cyanide.

In one embodiment, said cyano group-containing silicon compound is a trialkylsilyl cyanide.

In one embodiment, said trialkylsilyl cyanide is trimethylsilyl cyanide.

In one embodiment, said acid is sulfuric acid or comprises sulfuric acid.

In one embodiment, per molar equivalent 1-hydroxy-1,3,3,5,5-pentamethylcyclohexane from 1.5 to 2.5 molar equivalents sodium cyanide or potassium cyanide and from 3 to 7 molar equivalents sulfuric acid are employed.

In one embodiment, per molar equivalent 1-hydroxy-1,3,3,5,5-pentamethylcyclohexane from 1.0 to 2.0 molar equivalents trimethylsilyl cyanide and from 2 to 4 molar equivalents sulfuric acid are employed.

In one embodiment, in step (iv), an acid or a base is added to the mixture.

In one embodiment, steps (iii) and (iv) are performed as a one-pot-reaction.

In one embodiment, said reaction according to step (iii) is performed in a temperature range of from −20° C. to 30° C.

In one embodiment, said hydrolysis according to step (iv) is performed at a temperature of from 40° C. up to the reflux temperature of the mixture comprising 1-formamido-1,3,3,5,5-pentamethylcyclohexane.

In one embodiment, the method further comprises step (v):
  (v) converting 1-amino-1,3,3,5,5-pentamethylcyclohexane from step (iv) to a pharmaceutically acceptable salt thereof.

In one embodiment, the conversion is effected by hydrochloric acid or methanesulfonic acid.

In one embodiment, the process further comprises step (vi):
  (vi) crystallizing said pharmacologically acceptable salt formed in step (v).

In one embodiment, the invention relates to a method of preparing 1-amino-1,3,3,5,5-pentamethylcyclohexane or a pharmaceutically acceptable salt thereof, comprising steps (iii) and (iv):
  (iii) reacting 1-hydroxy-1,3,3,5,5-pentamethylcyclohexane with hydrogen cyanide in the presence of an acid, or with a compound that forms hydrogen cyanide in the presence of said acid, to yield a mixture comprising said acid and 1-formamido-1,3,3,5,5-pentamethylcyclohexane; and
  (iv) hydrolyzing the mixture of step (iii) to yield 1-amino-1,3,3,5,5-pentamethylcyclohexane.

In one embodiment, the process further comprises step (vii):
  (vii) subjecting gaseous compounds formed in any one of steps (iii) to (vi) to a scrubber.

DETAILED DESCRIPTION OF THE INVENTION

The present invention relates to a method of preparing 1-amino-1,3,3,5,5-pentamethylcyclohexane or a pharmaceutically acceptable salt thereof.

More specifically, the invention relates to a method of preparing 1-amino-1,3,3,5,5-pentamethylcyclohexane or a pharmaceutically acceptable salt thereof, comprising step (iv):
  (iv) hydrolyzing a mixture comprising an acid, 1-formamido-1,3,3,5,5-pentamethylcyclohexane and hydrogen cyanide to yield 1-amino-1,3,3,5,5-pentamethylcyclohexane.

In one embodiment the method of the present invention comprises prior to step (iv) step (iii):
  (iii) reacting 1-hydroxy-1,3,3,5,5-pentamethylcyclohexane with hydrogen cyanide in the presence of said acid, or with a compound that forms hydrogen cyanide in the presence of said acid, to yield a mixture comprising said acid, 1-formamido-1,3,3,5,5-pentamethylcyclohexane and hydrogen cyanide.

Contrary to the methods of the prior art, the formed 1-formamido-1,3,3,5,5-pentamethylcyclohexane may be used directly within step (iv), i.e. is neither isolated from the mixture of step (iii) nor purified nor isolated and purified.

Hydrogen cyanide as used in the Ritter reaction of step (iii) as the actual nitrile source may be provided from various sources.

In one embodiment, it may be employed as such, e.g. it may be fed in gaseous or liquefied form to a mixture comprising 1-hydroxy-1,3,3,5,5-pentamethylcyclohexane.

In one embodiment, hydrogen cyanide is employed in a molar excess with regard to one molar equivalent 1-hydroxy-1,3,3,5,5-pentamethylcyclohexane.

In one embodiment, per molar equivalent 1-hydroxy-1,3,3,5,5-pentamethylcyclohexane from 1.5 to 3 molar equivalents hydrogen cyanide are employed.

In another embodiment, hydrogen cyanide is generated in situ.

The term "in situ" means that in step (iii) instead of hydrogen cyanide as such a compound is employed that in the presence of said acid generates hydrogen cyanide, or from which hydrogen cyanide can be generated.

Said generation of hydrogen cyanide may be effected e.g. by decomposition of said compound, or e.g. by displacement reactions in said compound.

In one embodiment, said compound that forms hydrogen cyanide in the presence of said acid is a salt of hydrogen cyanide such as a salt of ammonia or an alkali metal.

In one embodiment, said salt is selected from the group consisting of ammonium cyanide, sodium cyanide, potassium cyanide.

Said generation of hydrogen cyanide may be effected by a displacement reaction of hydrogen cyanide in salts thereof by an acid that is a stronger acid than hydrogen cyanide itself that is a weak acid only. Such a displacement reaction of hydrogen cyanide from a salt thereof in general occurs if the acid acting on said salt has a $pK_a$ value that is lower than the $pK_a$ value of hydrogen cyanide.

In another embodiment, it is possible to employ suitable organic or organometallic compounds that are able to at least partially generate hydrogen cyanide in the presence of said acid.

In one embodiment, said organic or organometallic compound is a cyano group-containing silicon compound.

In one embodiment, said cyano group-containing silicon compound is a trialkylsilyl cyanide. In one embodiment, said trialkylsilylcyanide is trimethylsilyl cyanide (TMSCN).

It is also conceivable that organic nitriles at least partially generate hydrogen cyanide in the presence of an acid, wherein said hydrogen cyanide reacts in step (iii) with 1-hydroxy-1,3,3,5,5-pentamethylcyclohexane in the presence of said acid to yield a mixture comprising said acid and 1-formamido-1,3,3,5,5-pentamethylcyclohexane.

In one embodiment, said acid used in the Ritter reaction of step (iii) is selected from the group consisting of nitric acid, phosphoric acid, sulfuric acid, acetic acid, methanesulfonic acid, or is a mixture of two or more of said acids.

In one embodiment, sulfuric acid is used for performing said Ritter reaction according to step (iii).

In one embodiment, the used sulfuric acid is concentrated sulfuric acid.

In one embodiment, the used sulfuric acid has a content of at least 95% by weight based on the total amount of said acid.

In another embodiment, a, mixture of sulfuric acid and acetic acid is used for performing said Ritter reaction. Acetic acid may advantageously lower the viscosity of the mixture employed in step (iii).

In one embodiment, the acid used in the Ritter reaction of step (iii) is employed in a molar excess based on one molar equivalent 1-hydroxy-1,3,3,5,5-pentamethylcyclohexane.

In one embodiment, from 2 to 7 molar equivalents acid per one molar equivalent 1-hydroxy-1,3,3,5,5-pentamethylcyclohexane are employed.

In one embodiment, per molar equivalent 1-hydroxy-1,3,3,5,5-pentamethylcyclohexane from 1 to 3 molar equivalents hydrogen cyanide or from 1 to 3 molar equivalents of a compound that forms hydrogen cyanide in the presence of said acid are employed.

In a further embodiment, per molar equivalent 1-hydroxy-1,3,3,5,5-pentamethylcyclohexane from 1.5 to 2.5 molar equivalents sodium cyanide or potassium cyanide and from 3 to 7 molar equivalents sulfuric acid are employed.

In a specific embodiment, per molar equivalent 1-hydroxy-1,3,3,5,5-pentamethylcyclohexane about 2 molar equivalents sodium cyanide or potassium cyanide and about 5 molar equivalents sulfuric acid are employed.

In another embodiment, per molar equivalent 1-hydroxy-1,3,3,5,5-pentamethylcyclohexane from 1 to 2 molar equivalents trimethylsilyl cyanide and from 2 to 4 molar equivalents sulfuric acid are employed.

In a specific embodiment, per molar equivalent 1-hydroxy-1,3,3,5,5-pentamethylcyclohexane about 1.3 molar equivalents trimethylsilyl cyanide and about 3 molar equivalents sulfuric acid are employed.

In one embodiment, the temperature of the Ritter reaction in step (iii) is controlled. Said temperature should not be too high in order to avoid side reactions.

In one embodiment, the Ritter reaction according to step (iii) is performed in a temperature range of from −20° C. to 30° C., or from −15° C. to 20° C., or from −5° C. to 15° C.

In one embodiment, the reaction mixture in step (iii) may comprise a suitable organic solvent in order to prevent a solidification of said mixture due to the used low temperature and/or high concentration of the mixture.

In one embodiment, the used organic solvent is ethyl acetate, or the above mentioned acetic acid.

In one embodiment, the reaction according to step (iii) is performed such that a mixture of 1-hydroxy-1,3,3,5,5-pentamethlycyclohexane and hydrogen cyanide or a compound that forms hydrogen cyanide is provided, and said acid is added to said mixture such that the temperature may be kept in the desired temperature range.

In one embodiment, the formation of 1-formamido-1,3,3,5,5-pentamethylcyclohexane in the mixture according to step (iii) is e.g. monitored by commonly employed chromatographical methods. After the completion of the formation, step (iv) may be performed.

In one embodiment, in order to perform hydrolyzing step (iv), water already being contained in the mixture and/or water that has been generated in step (iii) may be used for performing hydrolysis step (iv).

In another embodiment, further water is added for performing hydrolysis step (iv).

In one embodiment, said hydrolyzing step is performed under the catalytic influence of an acid, i.e. under acidic conditions.

In one embodiment, said hydrolyzing step is catalyzed by the acid from step (iii) already being contained in said mixture.

In another embodiment, it is possible to add further acid, e.g. selected from the acids mentioned above.

In another embodiment, said hydrolyzing step (iv) is performed under basic conditions. In this embodiment, a base is added to a mixture comprising an acid and 1-formamido-1,3,3,5,5-pentamethylcyclohexane in order to set the pH value above 7. Suitable bases are e.g. alkali metal hydroxides such as sodium hydroxide or potassium hydroxide.

Accordingly, in one embodiment, in step (iv), an acid or a base is added to a mixture comprising the mixture obtained in step (iii).

Furthermore, in order to accelerate hydrolysis, step (iv) may be performed at elevated temperature.

In one embodiment, a temperature of from 40° C. up to the reflux temperature of the mixture comprising 1-formamido-1,3,3,5,5-pentamethylcyclohexane is employed.

In one embodiment, the mixture to be hydrolyzed in step (iv) is the mixture directly obtained in step (iii).

In one embodiment, after step (iii) has been performed, step (iv) is directly performed subsequent to step (iii).

In one embodiment, step (iv) is performed in the same reaction vessel as step (iii).

Accordingly, in one embodiment, steps (iii) and (iv) are performed as a one-pot-reaction.

The person skilled in the art will readily acknowledge that such one-pot-reaction allows for a particularly beneficial space-time yield.

If hydrolysis step (iv) is performed under acidic conditions, e.g. directly under the acidic conditions of the Ritter reaction in step (iii), the resulting 1-amino-1,3,3,5,5-pentamethylcyclohexane will be dissolved in the resulting mixture in the form of the corresponding salt.

In order to isolate the free amine, said mixture may subsequently be set with base to a pH above 7. The amine commonly separates from the mixture in the form of an organic layer and may be separated off. If necessary, the free amine may also be extracted by means of a suitable organic solvent such as methylene chloride, ether or petroleum ether. In order to further purify said amine, it may be subjected to distillation.

It was not foreseeable that despite the omission of a purification step of 1-formamido-1,3,3,5,5-pentamethylcyclohexane, the reaction sequence according to steps (iii) and (iv) results in a product having the required quality that allows for conversion to a pharmaceutically acceptable salt thereof. This is advantageous in view of an industrial realization.

In a further embodiment, 1-amino-1,3,3,5,5-pentamethylcyclohexane as prepared according to steps (iii) and (iv) is converted to a salt thereof by reaction with a suitable acid. Such reactions are basically known in the art, e.g. from the above referenced reaction scheme.

Accordingly, in one embodiment, the method further comprises step (v):

(v) converting 1-amino-1,3,3,5,5-pentamethylcyclohexane from step (iv) to a pharmaceutically acceptable salt thereof.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid. All these salts (or other similar salts) may be prepared by conventional means. The nature of the salt is not critical, provided that it is non-toxic and does not substantially interfere with the desired pharmacological activity.

The phrase "pharmaceutically acceptable", as used in connection with the compositions prepared according to the methods of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

In one embodiment, the conversion to a pharmaceutically acceptable salt is effected by hydrochloric acid or methanesulfonic acid.

In one embodiment, said pharmacologically acceptable salt formed in step (v) is crystallized for further purification.

Accordingly, the method according to the invention further comprises step (vi):

(vi) crystallizing said pharmacologically acceptable salt formed in step (v).

Suitable crystallizing methods are known in the art. Crystallization may be achieved by reducing the temperature of the reaction mixture of step (vi), or distilling off partially the solvent used in step (vi), or a combination of these methods.

In reaction steps (iii) and/or (iv), hydrogen cyanide is formed that, due to the reaction conditions, may at least partially be volatile. This means that said hydrogen cyanide may not only be present in dissolved form, but also in the gas phase.

Thus, in one embodiment, in order to facilitate a safe processing of the products formed in steps (iii) and (iv) and, optionally, also in step (vi), gaseous compounds formed in any one of said steps are subjected to a scrubber. Preferably, said scrupper is run with an aqueous base such as aqueous sodium hydroxide in order to remove from the process according to the invention any gaseous hydrogen cyanide or any other gaseous compounds that might be toxic.

Accordingly, said process according to the invention further comprises step (vii):

(vii) subjecting gaseous compounds formed in any one of steps (iii) to (vi) to a scrubber.

In one embodiment, the method comprises steps (iii) and (iv):

(iii) reacting 1-hydroxy-1,3,3,5,5-pentamethylcyclohexane with hydrogen cyanide in the presence of an acid, or with a compound that forms hydrogen cyanide in the presence of said acid, to yield a mixture comprising said acid and 1-formamido-1,3,3,5,5-pentamethylcyclohexane; and (iv) hydrolyzing the mixture of step (iii) to yield 1-amino-1,3,3,5,5-pentamethylcyclohexane.

EXAMPLES

Example 1

To a vigorously stirred solution of 1-hydroxy-1,3,3,5,5-pentamethylcyclohexane (3.4 g; 20 mmol) and trimethylsilyl cyanide (2.58 g; 26 mmol; 1.3 eq.) in ethyl acetate (4 ml), 95% sulfuric acid (3.2 ml; 60 mmol; 3.1 eq) are added during 1 hour keeping the temperature at −10° C. for 15 min, and then allowing the mixture to reach ambient temperature. After stirring at ambient temperature for 15 hours, the mixture is diluted with 20 ml ice water. Subsequently, the mixture is refluxed with stirring for 10 hours, cooled to ambient temperature, diluted with 40 ml water and 20 ml ether and neutralized with 20% aqueous sodium hydroxide until a pH of 10. The organic phase is separated and dried. Dry hydrogen chloride is passed through the solution until the ether becomes acidic. Solvent is removed and the residue is washed with ether to give 3.1 g Neramexane in the form of its hydrochloride.

Example 2

To a vigorously stirred solution of 1-hydroxy-1,3,3,5,5-pentamethylcyclohexane (3.4 g; 20 mmol) and sodium cyanide (1.96 g; 40 mmol; 2 eq.) and 5 ml acetic acid, 95% sulfuric acid (5.3 ml; 100 mmol; 5.15 eq) are added during 1 hour keeping the temperature at 10° C. for 30 min, and then allowing the mixture to reach ambient temperature. After stirring at ambient temperature for 17 hours, the mixture is diluted with 20 ml ice water. Subsequently, the mixture is refluxed with stirring for 10 hours, cooled to ambient temperature, diluted with 40 ml water and 20 ml ether and neutralized with 20% aqueous sodium hydroxide until a pH of 10. The organic phase is separated and dried. Dry hydrogen chloride is passed through the solution until the ether becomes acidic. Solvent is removed and the residue is washed with ether to give 2.24 g Neramexane in the form of its hydrochloride.

The invention claimed is:

1. A method of preparing 1-amino-1,3,3,5,5-pentamethylcyclohexane or a pharmaceutically acceptable salt thereof, comprising the following steps:

(iii) reacting 1-hydroxy-1,3,3,5,5-pentamethylcyclohexane with hydrogen cyanide in the presence of said acid, or with a compound that forms hydrogen cyanide in the presence of said acid, to yield a mixture comprising said acid, 1-formamido-1,3,3,5,5-pentamethylcyclohexane and hydrogen cyanide;

(iv) hydrolyzing the mixture comprising an acid, 1-formamido-1,3,3,5,5-pentamethylcyclohexane and hydrogen cyanide obtained in step (iii) to yield 1-amino-1,3,3,5,5-pentamethylcyclohexane; and, optionally, (v) converting the 1-amino-1,3,3,5,5-pentamethylcyclohexane from step (iv) to a pharmaceutically acceptable salt thereof.

2. The method according to claim 1, wherein the compound that forms hydrogen cyanide in the presence of said acid is a salt of hydrogen cyanide, or is a cyano group-containing silicon compound.

3. The method according to claim 2, wherein said salt of hydrogen cyanide is selected from ammonium cyanide, sodium cyanide, potassium cyanide, and said cyano group-containing compound is a trialkylsilyl cyanide.

4. The method according to claim 3, wherein said trialkylsilyl cyanide is trimethylsilyl cyanide.

5. The method according to claim 1, wherein the acid is sulfuric acid or comprises sulfuric acid.

6. The method according to claim 5, wherein per molar equivalent 1-hydroxy-1,3,3,5,5-pentamethylcyclohexane from 1.5 to 2.5 molar equivalents sodium cyanide or potassium cyanide and from 3 to 7 molar equivalents sulfuric acid are employed.

7. The method according to claim 5, wherein per molar equivalent 1-hydroxy-1,3,3,5,5-pentamethylcyclohexane from 1 to 2 molar equivalents trimethylsilyl cyanide and from 2 to 4 molar equivalents sulfuric acid are employed.

8. The method according to claim 1, wherein in step (iv) an acid or a base is added to the mixture.

9. The method according to claim 1, wherein steps (iii) and (iv) are performed as a one-pot-reaction.

10. The method according to claim 1, wherein the reaction according to step (iii) is performed in a temperature range of from −20° C. to 30° C.

11. The method according to claim 1, wherein the hydrolysis according to step (iv) is performed at a temperature of from 40° C. up to the reflux temperature of the mixture comprising 1-formamido-1,3,3,5,5-pentamethylcyclohexane.

12. The method according to claim 1,
wherein the 1-amino-1,3,3,5,5-pentamethylcyclohexane is converted to a pharmaceutically acceptable salt.

13. The method according to claim 12, wherein the conversion is effected by hydrochloric acid or methanesulfonic acid.

14. The method according to claim 12, further comprising step (vi):
(vi) crystallizing said pharmacologically acceptable salt formed in step (v).

15. A method of preparing 1-amino-1,3,3,5,5-pentamethylcyclohexane or a pharmaceutically acceptable salt thereof, comprising steps the following steps:

(iii) reacting 1-hydroxy-1,3,3,5,5-pentamethylcyclohexane with hydrogen cyanide in the presence of an acid, or with a compound that forms hydrogen cyanide in the presence of said acid, to yield a mixture comprising said acid and 1-formamido-1,3,3,5,5-pentamethylcyclohexane;

(iv) hydrolyzing the mixture of step (iii) to yield 1-amino-1,3,3,5,5-pentamethylcyclohexane; and optionally, (v) converting the 1-amino-1,3,3,5,5-pentamethylcyclohexane from step (iv) to a pharmaceutically acceptable salt thereof.

16. The method according to claim 1, further comprising step (vii):
(vii) subjecting gaseous compounds formed in step (iv) to a scrubber.

17. The method according to claim 14, further comprising step (vii):
(vii) subjecting gaseous compounds formed in any one of steps (iii) to (vi) to a scrubber.

18. The method according to claim 15, further comprising step (vii):
(vii) subjecting gaseous compounds formed in steps (iii) and/or (iv) to a scrubber.

* * * * *

UNITED STATES PATENT AND TRADEMARK OFFICE
CERTIFICATE OF CORRECTION

| | | |
|---|---|---|
| PATENT NO. | : 8,692,021 B2 | Page 1 of 1 |
| APPLICATION NO. | : 13/498432 | |
| DATED | : April 8, 2014 | |
| INVENTOR(S) | : Gold et al. | |

It is certified that error appears in the above-identified patent and that said Letters Patent is hereby corrected as shown below:

Title Page, Item [56] Other Publications, Chen, et al.: "1956" should be --1996--.

In the Claim

Column 10, Line 4 Claim 11 "1,3,3,5-pentamethylcyclohexane" should be --1,3,3,5,5-pentamethylcyclohexane--.

Signed and Sealed this
Twentieth Day of May, 2014

Michelle K. Lee
*Deputy Director of the United States Patent and Trademark Office*